(12) United States Patent
Rudser (10) Patent No.: US 10,940,250 B2
(45) Date of Patent: Mar. 9, 2021

(54) POWER SUPPLY WITH VEHICLE ADAPTER AND BATTERY

(71) Applicant: HeartWare, Inc., Mounds View, MN (US)

(72) Inventor: John Rudser, Miami, FL (US)

(73) Assignee: HeartWare, Inc., Miami Lakes, FL (US)

( * ) Notice: Subject to any disclaimer, the term of this patent is extended or adjusted under 35 U.S.C. 154(b) by 518 days.

(21) Appl. No.: 15/441,567

(22) Filed: Feb. 24, 2017

(65) Prior Publication Data

US 2017/0246366 A1 Aug. 31, 2017

Related U.S. Application Data

(60) Provisional application No. 62/299,747, filed on Feb. 25, 2016.

(51) Int. Cl.
*A61M 1/12* (2006.01)
*H02J 7/02* (2016.01)
(Continued)

(52) U.S. Cl.
CPC .......... *A61M 1/127* (2013.01); *A61M 1/1086* (2013.01); *A61M 1/122* (2014.02);
(Continued)

(58) Field of Classification Search
CPC .................................................. Y10T 307/625
See application file for complete search history.

(56) References Cited

U.S. PATENT DOCUMENTS 6,067,474 A * 5/2000 Schulman ............... H02J 50/10
607/57
6,122,181 A * 9/2000 Oughton, Jr. ........... H02J 9/061
307/66

(Continued)

FOREIGN PATENT DOCUMENTS

CN 1302469 A 7/2001
CN 103931077 A 7/2014

OTHER PUBLICATIONS

International Search Report and Written Opinion dated Jun. 27, 2017 for International Application No. PCT/US2017/019352, International Filing Date—Feb. 24, 2017 consisting of 10-pages.

(Continued)

*Primary Examiner* — Daniel Kessie
(74) *Attorney, Agent, or Firm* — Christopher & Weisberg, P.A.

(57) ABSTRACT

A control circuit for controlling a supply of power to an external electronics module for controlling an implanted device of the user, the control circuit electrically coupled to a switching circuit for controlling an electrical connection between an external power source, a battery, and an external electronics module, the control circuit further electrically coupled to a sensor for sensing at least one from the group consisting of a voltage and a current received from the external power source, the control circuit being configured to control the switching circuit to electrically disconnect the external electronics module from the external power source and electrically connect the external electronics module to the battery in response to a sensed fluctuation of at least one from the group consisting of voltage and current and electrically connect the external electronics module to the external power source and electrically disconnect the external (Continued)

electronics module from the battery when the fluctuation is not sensed.

15 Claims, 4 Drawing Sheets

(51) Int. Cl.
 *A61M 1/10* (2006.01)
 *A61N 1/378* (2006.01)
(52) U.S. Cl.
 CPC ...... *H02J 7/025* (2013.01); *A61M 2205/3317* (2013.01); *A61M 2205/8206* (2013.01); *A61M 2205/8243* (2013.01); *A61M 2205/8262* (2013.01); *A61N 1/3787* (2013.01)

(56) References Cited

U.S. PATENT DOCUMENTS

| | | | |
|---|---|---|---|
| 6,123,726 A | | 9/2000 | Mori et al. |
| 6,240,318 B1 * | | 5/2001 | Phillips ................ A61N 1/08 607/61 |
| 6,430,692 B1 * | | 8/2002 | Kimble ................ G06F 1/263 307/66 |
| 6,553,263 B1 * | | 4/2003 | Meadows ............ A61N 1/3787 607/61 |
| 7,295,878 B1 * | | 11/2007 | Meadows ............ A61N 1/3787 607/61 |
| 9,192,772 B1 * | | 11/2015 | Tsukamoto .......... A61N 1/3605 |
| 2006/0222533 A1 | | 10/2006 | Reeves et al. |
| 2008/0303480 A1 * | | 12/2008 | Prutchi ................ A61N 1/3787 320/108 |
| 2010/0036458 A1 * | | 2/2010 | Duftner .............. A61N 1/36038 607/57 |
| 2010/0241223 A1 | | 9/2010 | Lee et al. |
| 2010/0305692 A1 | | 12/2010 | Thomas et al. |
| 2011/0152600 A1 | | 6/2011 | Scott et al. |
| 2011/0159371 A1 * | | 6/2011 | Lyden ................ A61N 1/37512 429/231.95 |
| 2012/0053657 A1 | | 3/2012 | Parker et al. |
| 2012/0274271 A1 * | | 11/2012 | Thompson .............. H02J 5/005 320/108 |
| 2015/0249365 A1 | | 9/2015 | Shinohara |
| 2015/0290373 A1 | | 10/2015 | Rudser et al. |
| 2015/0290374 A1 | | 10/2015 | Bourque et al. |
| 2015/0290379 A1 | | 10/2015 | Shinohara |

OTHER PUBLICATIONS

China National Intellectual Property Administration, Notice of the First Office Action and Search Report, for corresponding CN Application No. 201780012585.0, dated Jun. 19, 2020, 29 pages.

* cited by examiner

POWER SUPPLY WITH VEHICLE ADAPTER AND BATTERY

CROSS-REFERENCE TO RELATED APPLICATION

This application is related to and claims priority to U.S. Provisional Patent Application Ser. No. 62/299,747, filed Feb. 25, 2016, entitled POWER SUPPLY WITH VEHICLE ADAPTER AND BATTERY, the entirety of which is incorporated herein by reference.

STATEMENT REGARDING FEDERALLY SPONSORED RESEARCH OR DEVELOPMENT n/a

TECHNICAL FIELD

The present invention relates to methods and devices for managing power supply to an implanted device, such as an implanted blood pump.

BACKGROUND

Transcutaneous energy transfer (TET) systems and percutaneous connectors may be used to supply power to devices such as heart pumps implanted internally within a human body. In the case of TET systems, an electromagnetic field generated by a transmitting coil outside the body can transmit power across a cutaneous (skin) barrier to a magnetic receiving coil implanted within the body. The receiving coil can then transfer the received power to the implanted device and to one or more batteries implanted within the body to charge the battery. In the case of percutaneous connection, an external power source may have a hard wire link, through a percutaneous connector, to supply power to an implantable electrical device.

These systems typically include an external electronics module which supplies power through a wireless or percutaneous connection. The external electronics module typically includes a battery and a connection to an external power source. External power sources may include, by way of example, an AC electrical outlet in a building or DC electrical outlet in a vehicle.

Some external power sources are subject to spikes, disruptions, or other changes, that adversely affect the systems' ability to effectively or efficiently power the implanted device. For example, in the case of a vehicle outlet, during normal operation of the vehicle, the implanted device may be powered via the vehicle's electrical outlet. However, in some vehicles, turning off the vehicle cuts power to the outlet, whereas in other vehicles power is always supplied to the outlet. Therefore, for a user whose device is plugged in to a vehicle outlet, it is not necessarily readily known to the user whether the device remains charged from the vehicle outlet when the vehicle is turned off. It is therefore desirable that the system be capable of notifying the user when power is or is not being supplied from the external power source. In many systems, the external electronics of the system is configured to issue a human-perceptible alert when the external power source is not electrically connected to the system. The alert may notify or otherwise remind the user that the implanted device is being powered by the battery, and that the user should make a connection to an external power source.

However, in some circumstances, the alert may be a nuisance or inconvenience to the user. For example, in many vehicles, power to the electrical outlet may be briefly interrupted or reduced when the vehicle's engine is started. In such a case, the user may be plugged into the vehicle outlet, but the brief disruption or fluctuation of power may be sufficient to trigger the alert, even though the device is electrically connected to an external power source. Such alerts due to brief disruptions or fluctuations in power supply may be an annoyance for the user.

SUMMARY

In one embodiment of the application, a control circuit for controlling a supply of power to an external electronics module mountable to a user for controlling an implanted device of the user, the control circuit electrically coupled to a switching circuit for controlling an electrical connection between an external power source, a battery, and an external electronics module, the control circuit further electrically coupled to a sensor for sensing at least one from the group consisting of a voltage and a current received from the external power source, the control circuit being configured to control the switching circuit to electrically disconnect the external electronics module from the external power source and electrically connect the external electronics module to the battery in response to a sensed fluctuation of at least one from the group consisting of voltage and current and electrically connect the external electronics module to the external power source and electrically disconnect the external electronics module from the battery when the fluctuation is not sensed.

In another aspect of this embodiment, the sensed fluctuation of at least one from the group consisting of the measured voltage and current is at least one from the group consisting of from the group consisting of: above a threshold maximum; being below a threshold minimum; increasing more than a threshold percentage, and decreasing more than a threshold percentage.

In another aspect of this embodiment, the external power source is a 12-volt vehicle battery, and wherein the sensed fluctuation is the measured voltage being below 9 volts.

In another aspect of this embodiment, the control circuit is configured to control the switching circuit to temporarily electrically disconnect the external electronics module from the external power source and temporarily electrically connect the external electronics module to the battery for a predetermined amount of time.

In another aspect of this embodiment, the control circuit is configured to control the switching circuit to electrically disconnect the external electronics module from the external power source and electrically connect the external electronics module to the battery until the control circuit determines to control the switching circuit to electrically connect the external electronics module to the external power source based on a subsequent measurement of the at least one from the group consisting of voltage and current received from the external power source.

In another embodiment, an apparatus for adapting power from an outlet of a vehicle includes a control circuit for controlling the supply of power to an external electronics module mountable to a user for controlling an implanted device of the user, the control circuit electrically coupled to a switching circuit for controlling an electrical connection between an external power source, a battery, and an external electronics module, the control circuit further electrically coupled to a sensor for sensing at least one from the group consisting of a voltage and a current received from the external power source, the control circuit being configured to control the switching circuit to: electrically disconnect the external electronics module from the external power source and electrically connect the external electronics module to the battery in response to a sensed fluctuation of the sensed at least one from the group consisting of voltage and current and electrically connect the external electronics module to the external power source and electrically disconnect the external electronics module from the battery when the fluctuation is not sensed. The apparatus is electrically coupled between the external power source and an external electronics module.

In another aspect of this embodiment, the battery, switching circuit, and control circuit are contained in a common housing.

In another aspect of this embodiment, the apparatus further includes an adapter for at least one from the group consisting of increasing and decreasing a voltage and current received from the outlet to a desired level.

In another aspect of this embodiment, the battery is rechargeable and electrically coupled to the adapter, the battery being charged by the outlet when the battery is not electrically connected to the external electronics module.

In another aspect of this embodiment, the adapter, battery, switching circuit and control circuit are contained in a common housing.

In another aspect of this embodiment, the apparatus is adapted to provide an electrical connection to a vehicle battery through a vehicle outlet.

In yet another embodiment, a system for controlling the supply of power to an implanted device includes an apparatus including a control circuit for controlling the supply of power to an external electronics module mountable to a user for controlling an implanted device of the user, the control circuit electrically coupled to a switching circuit for controlling an electrical connection between an external power source, a battery, and an external electronics module, the control circuit further electrically coupled to a sensor for sensing at least one from the group consisting of a voltage and a current received from the external power source, the control circuit being configured to control the switching circuit to: electrically disconnect the external electronics module from the external power source and electrically connect the external electronics module to the battery in response to a sensed fluctuation of the sensed at least one from the group consisting of voltage and current and electrically connect the external electronics module to the external power source and electrically disconnect the external electronics module from the battery when the fluctuation is not sensed. The apparatus is electrically coupled between the external power source and an external electronics module. An external electronics module is electrically coupled to the apparatus and mountable to a user of the implanted device. The external module includes an external electronics module controller for determining whether an amount of at least one from the group consisting of current and voltage received from the module is sufficient to power the implanted device. A second battery is included. A switch for switching between providing power from the apparatus to the implanted device and providing power from the second battery to the implanted device in response to the determination of the external electronics module controller is included. An alert module for notifying the user when power is provided from the second battery is included.

In another aspect of this embodiment, the battery is adapted to provide the amount of at least one from the group consisting of current and voltage sufficient to power the implanted device, and when the battery is providing power from the apparatus to the external electronics module, the switch provides power from the apparatus to the implanted device.

In yet another embodiment, a method of controlling the supply of power to an external module mountable to a user of an implanted device, the external module providing power to the implanted device, includes, at a control circuit, detecting a fluctuation in the level of power provided from an external power supply. In response to the detection, the control circuit controlling a switching circuit to electrically disconnect the external module from the external power source and electrically connect the external module to a battery coupled to the switching circuit in response to a detected fluctuation. When no fluctuation is detected, the external module is electrically connected to the external power source.

In another aspect of this embodiment, detecting a fluctuation includes detecting the power provided from the external power supply at least one from the group consisting of the group consisting of: exceeding a threshold maximum, dropping below a threshold minimum, and increasing or decreasing by more than a threshold percentage.

In another aspect of this embodiment, the switching circuit is controlled to electrically disconnect the external module from the external power source for a predetermined amount of time, and the control circuit determines whether there is a fluctuation remains after the predetermined amount of time.

In another aspect of this embodiment, the method further includes at the control circuit, determining that power is being provided from the external power source and that the fluctuation has cleared, and in response, controlling the switching circuit to electrically connect the implanted electrical device to the external power source.

In yet another embodiment, a method of controlling issuance of alert indicating disconnection of an external power source from an implanted medical device includes detecting a disruption of power being provided from the external power source. A switching circuit is controlled to electrically disconnect the implanted medical device from the implanted device and electrically connect a backup power source to the implanted medical device, the backup power source has an amount of charge sufficient to power the implanted device for less than between five seconds. In the event of a disruption of power longer than the amount of charge to power the implanted device, the disruption of power results in issuance of the alert, and in the event of a disruption of power shorter than the five seconds, the backup power source prevents the alert from issuing.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

The present disclosure provides for a device and method that yields a relatively steady supply of power without the spikes or fluctuations commonly associated with external power supply systems, such that the above described false or nuisance alerts are avoided.

Figure 1:
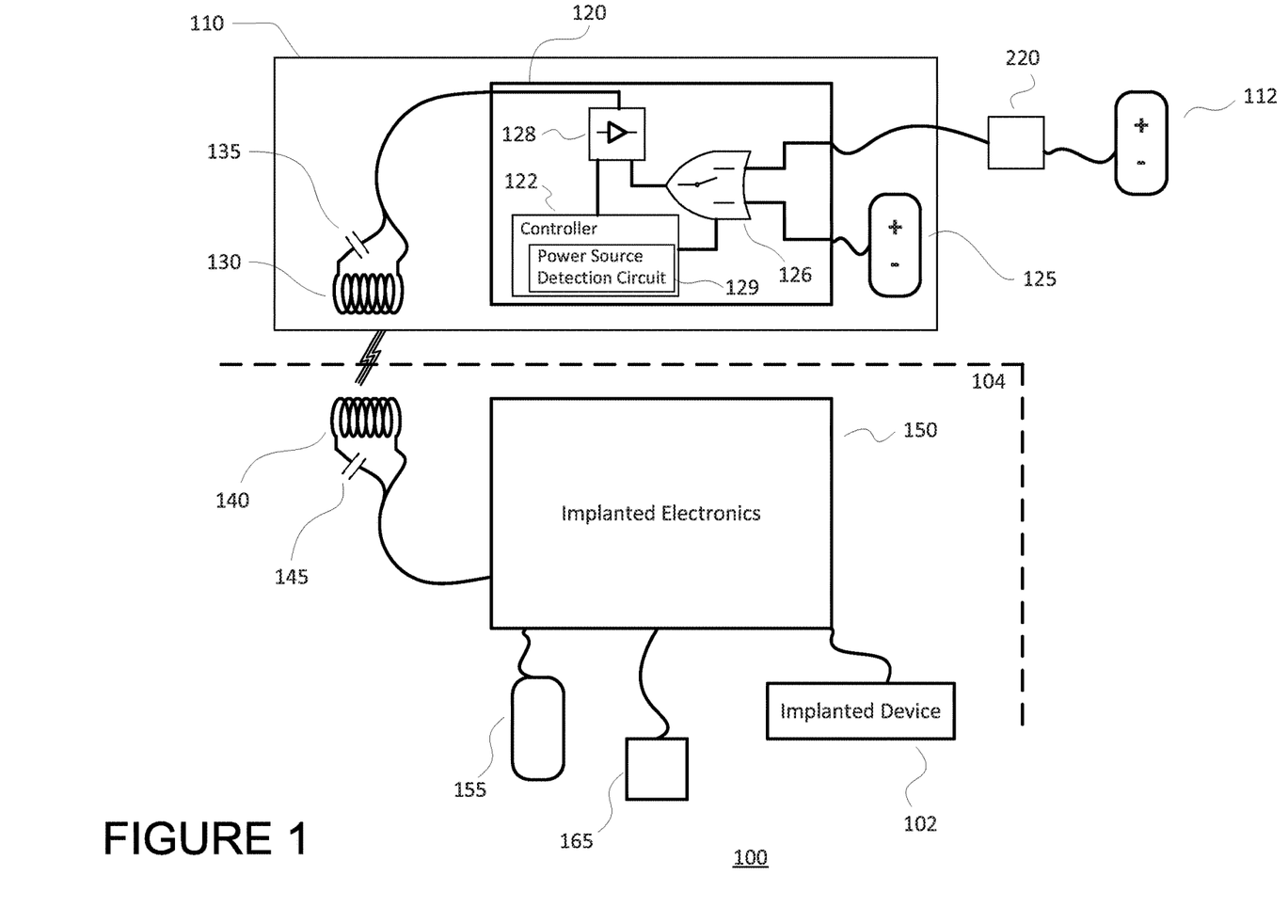
FIG. 1 is a functional diagram of a system in accordance with an aspect of the present disclosure.

FIG. 1 schematically illustrates an example system 100 including both external electronics 120 mounted outside the body of a human or animal patient 104, as well as internal or implanted electronics 150 mounted within the body of the patient 104. The example system of FIG. 1 is a TET system, although the present disclosure is similarly applicable to other systems providing power transfer via a percutaneous connection. The external electronics 120 are electrically coupled to one or more power sources, including, for example, a battery 125 associated with the external electronics 120, and an external power source 112 (such as AC power from a building, or DC power from a car battery). The external electronics 120 are also electrically coupled to an external primary coil 130, and the implanted electronics 150 are electrically coupled to an internal or implanted secondary coil 140. The external and implanted coils 130 and 140 are inductively coupled to one another through an electromagnetic field in order to transfer energy wirelessly therebetween.

Based on instructions from the controller 122, the power source selection circuitry 126 outputs power from one of the battery and external power source to an input of drive circuit 128. The drive circuit 128 amplifies the output power. The amplified power is then provided to the external coil 130. The external coil 130 is coupled to additional circuitry such as one or more capacitors 135 that form a resonant circuit with the external coil 130. The external coil 130 generates an electromagnetic field which inductively couples to the implanted coil 140 at the resonant frequency of the tuned resonant circuits.

In the example of FIG. 1, the external coil 130 is housed in a common external module 110 together with the external electronics 120, whereas the implanted coil 140 and implanted electronics 150 are not housed together. The external electronics 120 may further include control circuitry 122 for determining and executing instructions for controlling the drive circuitry in order, as well as a power source determination circuit 129 for determining a source of power for driving the external coil 130, to control the wireless transfer of energy between the external and implanted coils. The control circuitry 120 may include a microcontroller capable of setting the pulse width and/or frequency of transmission, controlling selection of the power source, driving the external coil 130, etc. Determinations made by the control circuitry 122 may be based on signals received from telemetry circuitry, from external sensors 115, and/or from inputs provided at a user interface of the external module 110. In response to the source determination circuit 129 determining that the current source of power is the battery 125, the external electronics may output an alert notifying the user of the device that the device is not electrically connected to an external power supply (e.g., source 112).

The implanted electronics 150 are electrically coupled to an implanted battery 155 and to the implanted electrical device 102. Energy received at the implanted coil 140 is stored in the implanted battery 155, provided to the implanted medical device 102, or both, via the implanted electronics 150. Additionally, energy stored at the implanted battery may be provided to the implanted electrical device 102 via the implanted electronics 150. The implanted electronics 150 may also be electrically coupled to internal sensing devices 165.

The implanted electronics 150 convert AC power generated at the implanted coil 140 to DC power, adjust the voltage level of the converted DC power (or power from the implanted battery 155) and provide the adjusted power to the implanted device 102. The implanted electronics 150 may further control an efficiency of the inductive coupling between the external and implanted coils 130 and 140, such as by instructing an adjustment in the resonant frequency of resonant circuit components 145 in the implanted coil 140. As with the external circuitry 120, such determinations at the implanted circuitry may be based on RF telemetry signals as well information received from the internal sensors 165.

Figure 2:
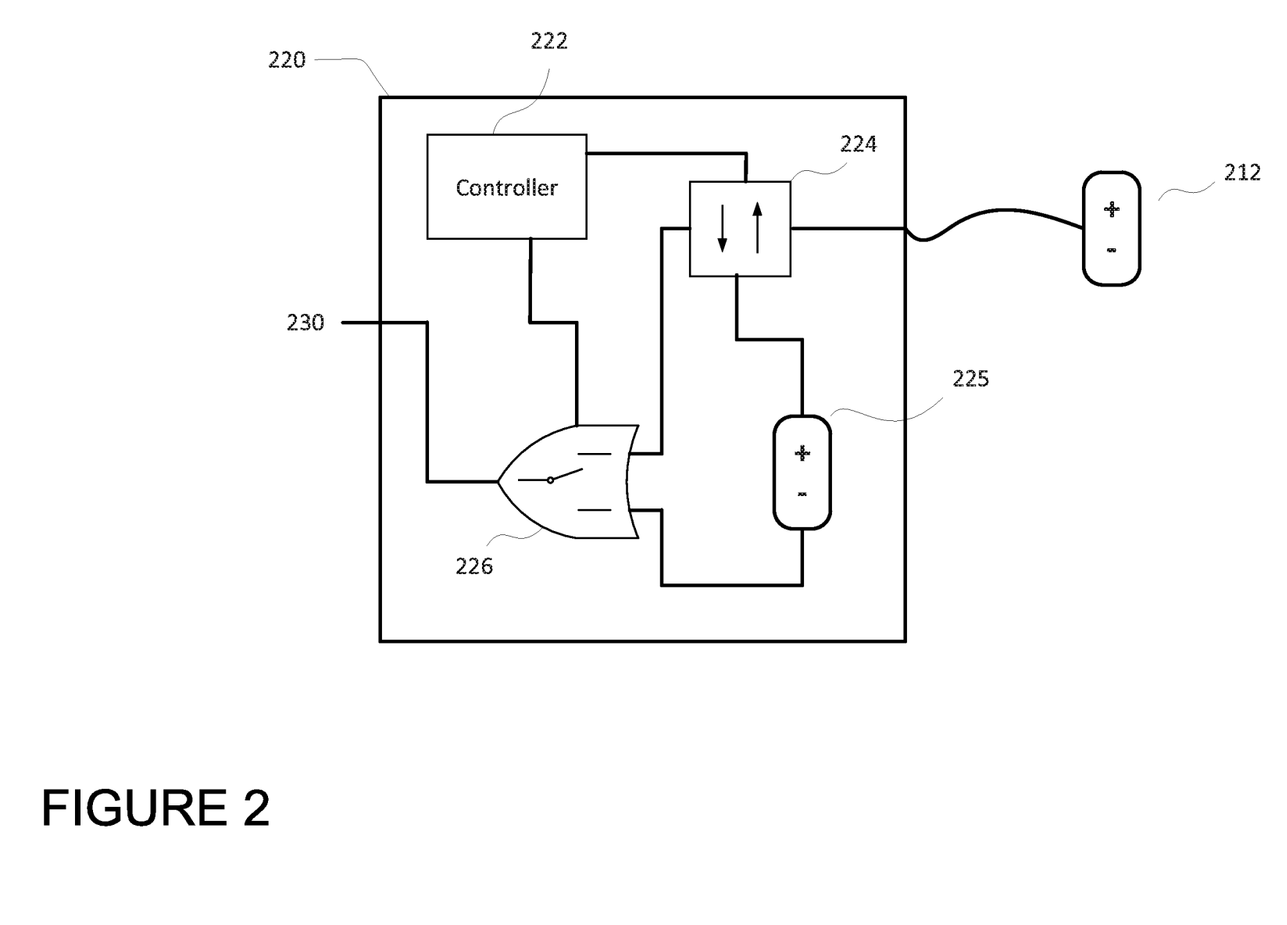
FIG. 2 is a functional diagram of an example adapter module of the system of FIG. 1 in accordance with an aspect of the disclosure.

In the example of FIG. 1, the external electronics 120 are connected to an external power source 112. In the case of a car battery or other power source subject to fluctuations, it may be preferable to include a power adapter 220 between the external power source and external electronics. FIG. 2 schematically illustrates an example adapter 220. The adapter of FIG. 2 includes an adapter 224, as well as other circuitry, and is therefore referred to comprehensively as a vehicle adapter module 220, although it could be a module for adapting power from sources other than in vehicles. The vehicle adapter module 220 includes an adapter 224, as well as a control circuit 222, battery 225, and power source switching circuit 226. The components of the vehicle adapter module 220 may be contained in a common housing. The vehicle adapter module 220 may electrically interface (e.g., plug into, be plugged into, or otherwise electrically connect to) a vehicle power outlet 212 and an external module 230 for powering an implanted medical device.

In the example of FIG. 2, the adapter 224 may be a buck-boost converter configured to receive electrical power from the vehicle power outlet 212, and to convert the received power to a desired power level (e.g., desired DC voltage). The desired power level may depend on the particular implanted device being powered by the external module 230.

The battery 225 may store an amount of charge sufficient to damp any fluctuations of power from the outlet 212. In some cases, this may be enough to power the implanted device for a few seconds, for example, 3 to 5 seconds, until power from the outlet returns to its normal state. In other cases, the battery 225 may store charge sufficient to power the implanted device for more than just a few seconds (e.g., about an hour). For instance, if the external electronics 120 are plugged into the adapter port of a vehicle, and the adapter port only supplies power when the vehicle is turned on, then the battery 225 may be relied on to power the implanted device from the time the adapter is plugged into the port until the vehicle is turned on.

The battery 225 may be a rechargeable battery. The adapter 224 may provide for at least a portion of the power from the outlet 212 to be provided to the battery 225. Thus, when power is being received from the outlet, the battery may be recharged by the power received from the outlet 212. The control circuit 222 is operable to receive a measurement of power being received from the vehicle power outlet 212. The measurement may, for instance, be one of a current or voltage sensed at the adapter 224. If there is a change in the measured voltage or current (e.g., exceeding a threshold maximum, going below a threshold minimum, increasing or decreasing by more than a threshold percentage), the control circuit 222 may determine the presence of a power fluctuation from the outlet 212. For instance, in the case of a 12-volt vehicle battery, the control circuit may react to a sensed voltage below about 9 volts. In response, the control circuit may instruct the switching circuit 226 to electrically disconnect the external module 230 from the outlet 212 and instead electrically connect the external module 230 to the battery 225.

In some cases, the control circuit 222 may instruct the switching circuit 226 to temporarily switch from the outlet 212 to the battery 225 for a predetermined amount of time, after which the switching circuit 226 may switch back to the outlet 212. Alternatively, the control circuit 222 may instruct the switching circuit 226 to switch indefinitely (e.g., until instructed to switch back to the outlet). In either case, the control circuit 222 may continue to monitor current and/or voltage at the adaptor, and if the current and/or voltage is determined to not have fluctuations, the switching circuit 226 may resume electrically connecting the outlet 212 to the external module 230. In some cases, this may involve the control circuit 222 not providing any instruction to the switching circuit 226, such that after the predetermined amount of time, the switching circuit 226 reverts to electrically connecting the outlet 212 and external module 225. Alternatively, where the switching circuit 226 was previously instructed to switch electrical connections indefinitely, the control circuit 222 may instruct the switching circuit to switch back to electrically connecting the outlet 212 and external module 225

Switching to battery 225 power may provide a temporary charge until the battery 225 is depleted. Although the battery may deplete relatively quickly (as compared to the battery 125 associated with the external electronics 130), the power stored therein may be enough to suppress any detection of a change in power source by the power source detection circuit 129, since the power from the battery 225 will appear to the power source detection circuit 129 to be power from an external source. Thus, in cases of brief fluctuations in power, the battery may prevent the triggering on an unnecessary alert by the external electronics 130, but in the event of a longer outage (e.g., indicative that the device is disconnected from the vehicle power), the battery 225 will deplete and the power source detection circuit 129 will trigger the desired alert.

Figure 3:
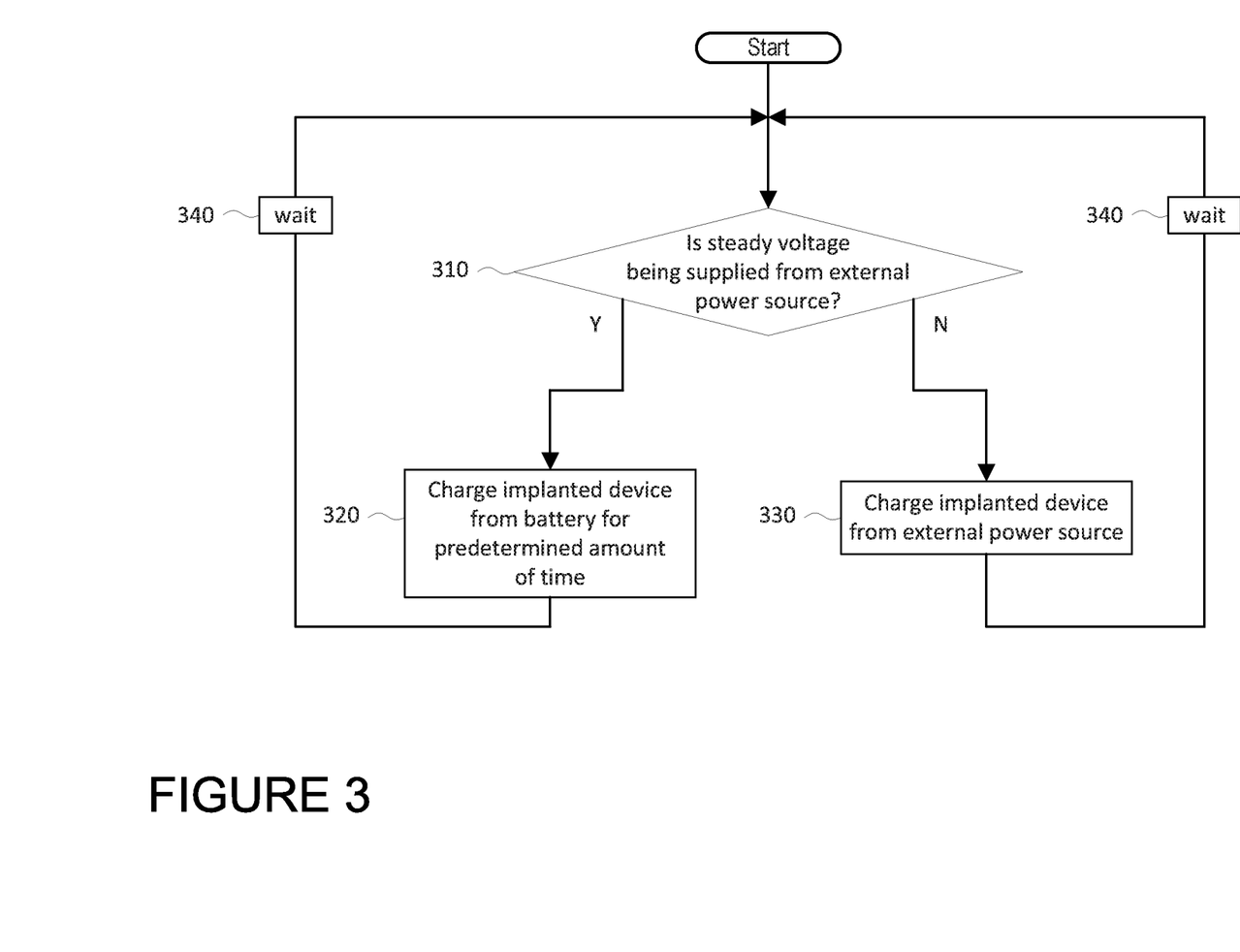
FIG. 3 is a flow diagram of an example method in accordance with an aspect of the disclosure.

FIG. 3 is a flowchart depicting an example routine 300 for controlling the supply of power to an implanted device. The example routine may be particularly beneficial for managing power supply during temporary spikes or dips in the external power supply in accordance with the above disclosure. Routine 300 may begin at 310, in which a control circuit determines whether steady voltage is or is not being supplied from an external power source to the implanted device. If an irregularity (e.g., dip, spike) in voltage from the external power source is detected, it may be determined that steady voltage is not being supplied, in which case the routine 300 may proceed to 320 and the implanted device is powered from a battery instead of from the external power supply for a predetermined amount of time. The battery may help to damp the irregularities (e.g., dips, spikes) in the external power supply. If no irregularity is detected, then it may be determined that steady voltage is being supplied, in which case the routine 300 may proceed to 330 with the implanted device being charged from the external power supply.

The above described routine may be repeatedly performed by the control circuit. The control circuit may be configured to repeat the process after the predetermined amount of time (wait 340). Thus, if the external power source experiences a momentary spike or dip in power, the control circuit may temporarily proceed to 320 with charging from the battery for the predetermined amount of time, and then switch back charging from the external power source at 330. Thus, the control circuit may reduce or even minimize battery usage in situations where the external power supply is available to provide power to the implanted device. In turn, minimizing battery usage allows for the battery used in the routine 300 to be relatively small, as compared to a battery for powering an implanted device for an extended duration of time.

Figure 4:
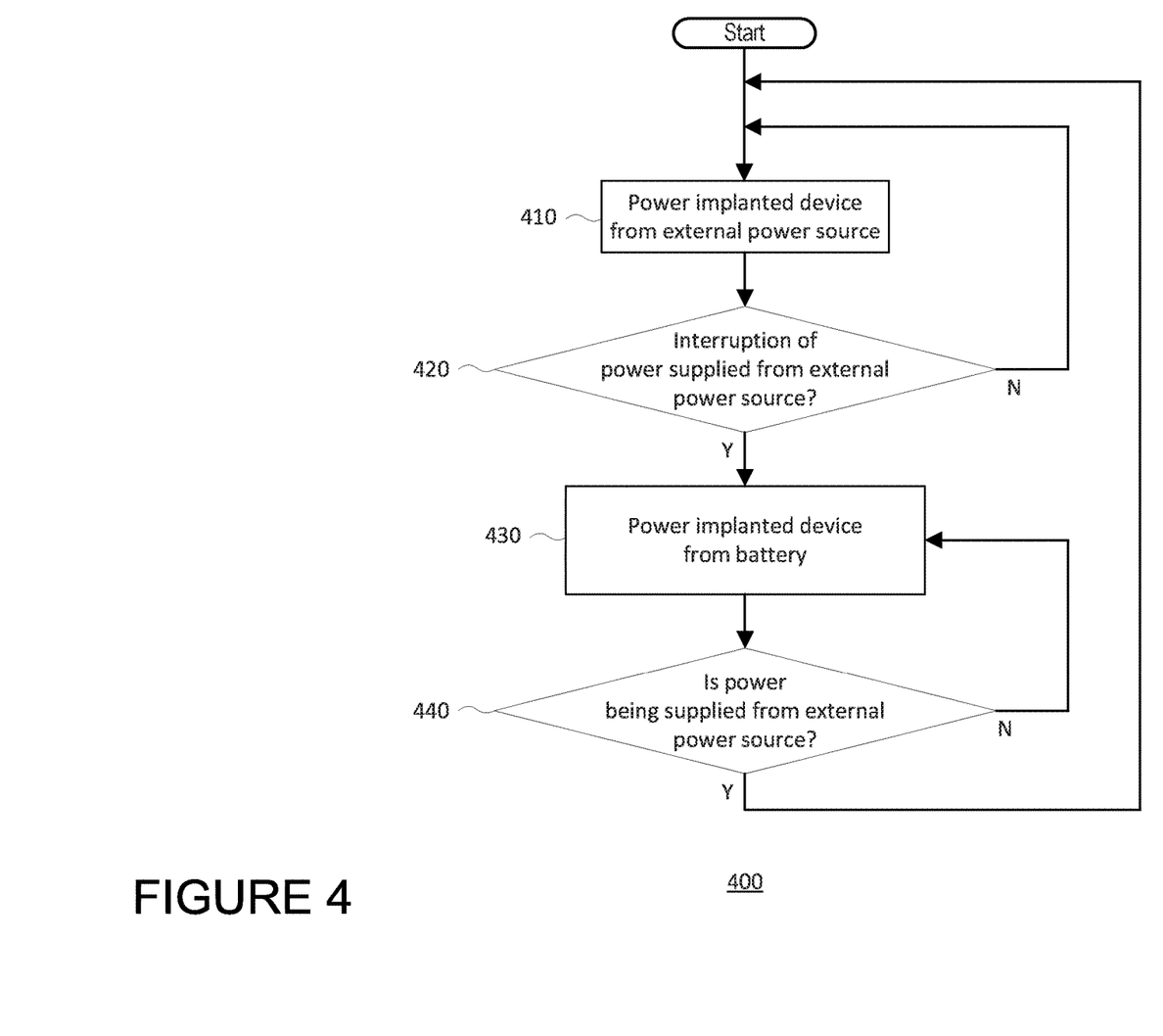
FIG. 4 is another flow diagram of an example method in accordance with an aspect of the disclosure.

FIG. 4 is a flowchart depicting another example of a routine 400 for controlling power supply. At 410, the implanted device is powered from the external power source. At 420, the control circuit determines whether there is an interruption in the supply of power from the external power source (e.g., a sensed voltage being below a predetermined threshold). If there is no interruption, the routine 400 reverts to 410, thereby continuing to provide power from the external power source. If there is an interruption, then at 430, power supply is switched to the battery such that the implanted device is powered from the battery. At 440, the control circuit determines whether there is a resumption of power being supplied from the external power source, in which case operations would continue at 410 with power being provided from external power source. The determination at 440 may be automatically triggered by reestablishing an electrical connection with the external power source. If no power is being provided from the external power source, operations may remain at 430 with power being supplied by the battery.

As with the routine of FIG. 3, the routine 400 of FIG. 4 may be repeatedly performed, such that the control circuit repeatedly determines to switch, and instructs a switching device to switch, between external power and battery power as the external power source is connected and disconnected. Thus, in a case where a user plugs in the adapter to a vehicle outlet before turning on the vehicle, the control circuit may determine to provide battery power until the vehicle is turned on. Also, in a case where the vehicle is turned on and the user repeatedly attempts to start a vehicle's engine, the control circuit may repeatedly switch between battery power (during start attempts) and vehicle power (between start attempts).

The examples of FIGS. 3 and 4 have been described generally in terms of connection to an implanted device. As shown in FIG. 2, the electrical connection controlled by the control circuit may be more specifically an electrical connection to an external module of an implanted device.

In addition to the routines of FIGS. 3 and 4, the control circuit 222 of the adapter module 220 may also prevent the external electronics 130 from triggering an alert by providing a notification to the external electronics indicating that the implanted device is still electrically connected to the external power source even though sufficient power is temporarily disrupted. The control circuit 222 may determine that the external power source 112 is still connected based on a detection of a pin connection and/or a minimal amount of voltage or current (even if not enough to power the device or charge the battery) 225 being sensed at the adapter 224. Based on this determination, the control circuit 222 instructs the external electronics 130 to override providing an alert, so the user is not inconvenienced. Such a notification may be beneficial in situations where the temporary disruption of power lasts longer than normal (e.g., attempted car start on cold day) and the adapter module battery 225 is depleted during the duration of the disruption.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended paragraphs.

What is claimed is:

1. A control circuit for controlling a supply of power to an external electronics module mountable to a user for controlling an implanted device of the user, the control circuit electrically coupled to a switching circuit for controlling an electrical connection between an external power source, a battery, and an external electronics module, the control circuit further electrically coupled to a sensor for sensing at least one from the group consisting of a voltage and a current received from the external power source, the control circuit being configured to control the switching circuit to:

electrically disconnect the external electronics module from the external power source, and electrically connect the external electronics module to the battery in response to a sensed fluctuation of the sensed at least one from the group consisting of voltage and current, the external electronics module including an alert module configured to issue at least one of an audible and a visual alert to the user when the external electronics module is not electrically connected to the external power source, the external electronics module being connected to a power adapter including a buck-boost converter, a controller, a switching circuit and another battery which stores an amount of charge sufficient to damp fluctuations of the power from the outlet;

the controller comparing a voltage from the back-boost converter coupled with the external power source with the another battery located within the adapter, and when its determined to not have fluctuations, the switching circuit resumes electrically connecting the external power module;

electrically connect the external electronics module to the external power source and electrically disconnect the external electronics module from the battery when the fluctuation is not sensed, the control circuit being configured to deactivate the alert module when the control circuit detects that power is being provided from the external power source; and the external electronics module and the battery are each contained in a common portable housing carriable by the user.

2. The control circuit of claim 1, wherein the sensed fluctuation of at least one from the group consisting of the measured voltage and current is at least one from the group consisting of:

above a threshold maximum;
being below a threshold minimum;
increasing more than a threshold percentage and decreasing more than a threshold percentage.

3. The control circuit of claim 2, wherein the external power source is a 12-volt vehicle battery, and wherein the sensed fluctuation is the measured voltage being below 9 volts.

4. The control circuit of claim 1, wherein the control circuit is configured to control the switching circuit to temporarily electrically disconnect the external electronics module from the external power source and temporarily electrically connect the external electronics module to the battery for a predetermined amount of time.

5. The control circuit of claim 1, wherein the control circuit is configured to control the switching circuit to electrically disconnect the external electronics module from the external power source and electrically connect the external electronics module to the battery until the control circuit determines to control the switching circuit to electrically connect the external electronics module to the external power source based on a subsequent measurement of the at least one from the group consisting of voltage and current received from the external power source.

6. An apparatus for adapting power from an outlet of a vehicle, the apparatus comprising:

a control circuit for controlling the supply of power to an external electronics module mountable to a user for controlling an implanted device of the user, the control circuit electrically coupled to a switching circuit for controlling an electrical connection between an external power source, a battery, and an external electronics module, the control circuit further electrically coupled to a sensor for sensing at least one from the group consisting of a voltage and a current received from the external power source, the control circuit being configured to control the switching circuit to:

electrically disconnect the external electronics module from the external power source and electrically connect the external electronics module to the battery in response to a sensed fluctuation of the sensed at least one from the group consisting of voltage and current, the external electronics module including an alert module configured to issue at least one of an audible and visual alert to the user when the external electronics module is not electrically connected to the external power source, the external electronics module being connected to a power adapter including a buck-boost converter, a controller, a switching circuit and another battery which stores an amount of charge sufficient to damp fluctuations of the power from the outlet; the controller comparing a voltage from the back-boost converter coupled with the external power source with the another battery located within the power adapter, and when its determined to not have fluctuations, the switching circuit resumes electrically connecting the external power module;

electrically connect the external electronics module to the external power source and electrically disconnect the external electronics module from the battery when the fluctuation is not sensed, the control circuit being configured to deactivate the alert module when the control circuit detects that power is being provided from the external power source;

the apparatus being electrically coupled between the external power source and an external electronics module; and the battery, switching circuit, and the control circuit are contained in a common housing carriable by the user.

7. The apparatus of claim 6, further comprising an adapter for at least one from the group consisting of increasing and decreasing a voltage and current received from the outlet to a desired level.

8. The apparatus of claim 7, wherein the battery is rechargeable and electrically coupled to the adapter, the battery being charged by the outlet when the battery is not electrically connected to the external electronics module.

9. The apparatus of claim 8, wherein the adapter, the battery, a second battery, the switching circuit and the control circuit are contained in a common housing.

10. The apparatus of claim 6, wherein the apparatus is adapted to provide an electrical connection to a vehicle battery through a vehicle outlet.

11. A system for controlling a supply of power to an implanted device, the system comprising:
an apparatus including:
a control circuit for controlling the supply of power to an external electronics module mountable to a user for controlling an implanted device of the user, the control circuit electrically coupled to a switching circuit for controlling an electrical connection between an external power source, a battery, and an external electronics module, the control circuit further electrically coupled to a sensor for sensing at least one from the group consisting of a voltage and a current received from the external power source, the control circuit being configured to control the switching circuit to:
electrically disconnect the external electronics module from the external power source and electrically connect the external electronics module to the battery in response to a sensed fluctuation of at least one from the group consisting of voltage and current, the external electronics module being connected to a power adapter including a buck-boost converter, a controller, a switching circuit and another battery which stores an amount of charge sufficient to damp fluctuations of the power from the outlet; the controller comparing a voltage from the back-boost converter coupled with the external power source with the another battery located within the power adapter, and when its determined to not have fluctuations, the switching circuit resumes electrically connecting the external power module;
electrically connect the external electronics module to the external power source and electrically disconnect the external electronics module from the battery when the fluctuation is not sensed; and
the apparatus being electrically coupled between the external power source and an external electronics module;
the control circuit, the switching circuit, the battery, the external electronics module, and the sensor are contained in a common housing carriable by the user,
the external electronics module electrically coupled to the apparatus and mountable to a user of the implanted device, the external electronics module comprises:
an external electronics module controller for determining whether an amount of at least one from the group consisting of current and voltage received from the module is sufficient to power the implanted device;
a switch for switching between providing power from the apparatus to the implanted device and providing power from the battery to the implanted device, in response to the determination of the external electronics module controller; and
an alert module configured to issue at least one of an audible and visual alert to the user when the external electronics module is not electrically connected to the external power source, the control circuit of the apparatus being configured to deactivate the alert module when the control circuit detects that power is being provided from the external power source.

12. A method of controlling the supply of power to an external electronics module mountable to a user of an implanted device, the external electronics module providing power to the implanted device, the method comprising:
at a control circuit, detecting a fluctuation in the level of power provided from an external power source;
in response to the detection, the control circuit controlling a switching circuit to electrically disconnect the external electronics module from the external power source and electrically connect the external electronics module to a battery coupled to the switching circuit in response to a detected fluctuation; the external electronics module being connected to a power adapter including a buck-boost converter, a controller, a switching circuit and another battery which stores an amount of charge sufficient to damp fluctuations of the power from the outlet; the controller comparing a voltage from the back-boost converter coupled with the external power source with the another battery located within the adapter, and when its determined to not have fluctuations, the switching circuit resumes electrically connecting the external power module;
issuing an alert to the user from the external electronics module when the external electronics module is not electrically connected to the external power source;
when no fluctuation is detected, the external electronics module is electrically connected to the external power source;
deactivating the alert when the control circuit detects that power is being provided from the external power source; and
the control circuit, the switching circuit, and the battery are contained in a common housing carriable by the user.

13. The method of claim 12, wherein detecting a fluctuation includes detecting the power provided from the external power source from at least one from the group consisting of:
exceeding a threshold maximum,
dropping below a threshold minimum, and
increasing or decreasing by more than a threshold percentage.

14. The method of claim 12, wherein the switching circuit is controlled to electrically disconnect the external electronics module from the external power source for a predetermined amount of time, and the control circuit determines whether there is a fluctuation remains after the predetermined amount of time.

15. The method of claim 12, further including, at the control circuit, determining that power is being provided from the external power source and that the fluctuation has cleared, and in response, controlling the switching circuit to electrically connect the implanted device to the external power source.

* * * * *